Figure 1:
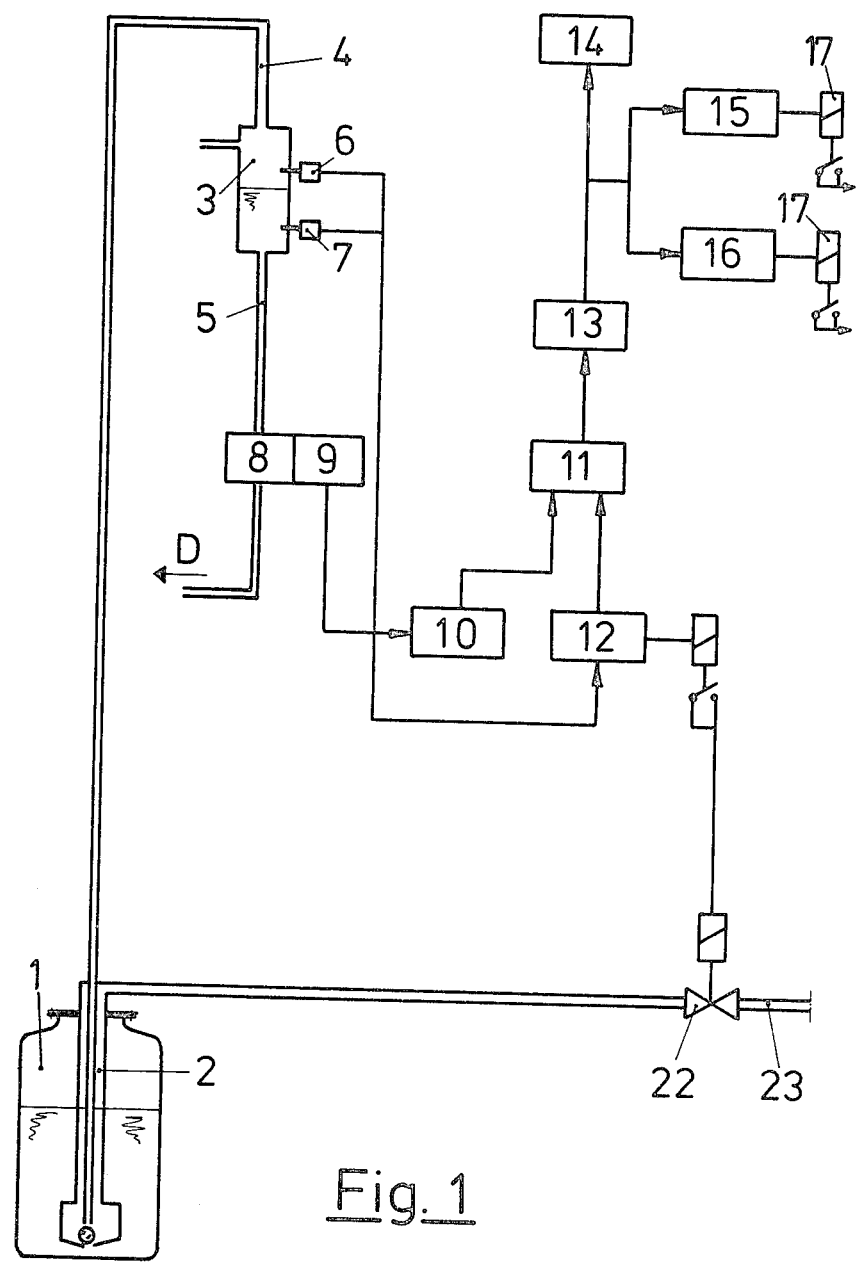

United States Patent [19]

Buschmann

[11] 4,232,802
[45] Nov. 11, 1980

[54] APPARATUS FOR PULSEWISE DISPENSATION OF VERY SMALL AMOUNTS OF LIQUID, PARTICULARLY $H_2O_2$

[75] Inventor: Gerhard Buschmann, Düsseldorf, Fed. Rep. of Germany

[73] Assignee: Jagenberg-Werke Aktiengesellschaft, Düsseldorf, Fed. Rep. of Germany

[21] Appl. No.: 971,778

[22] Filed: Dec. 21, 1978

[30] Foreign Application Priority Data

Dec. 24, 1977 [DE] Fed. Rep. of Germany ....... 2757897

[51] Int. Cl.³ .............................................. B67D 5/08
[52] U.S. Cl. ........................................ 222/56; 222/64; 222/334; 137/212; 222/394; 417/138
[58] Field of Search ........................ 222/52, 56, 63, 64, 222/67, 68, 334, 333, 394, 396, 397, 399, 400.7, 464; 417/138, 145, 147; 128/214 F, 214 E, DIG. 12, DIG. 13, DIG. 3; 137/209, 212

[56] References Cited

U.S. PATENT DOCUMENTS

| | | | |
|---|---|---|---|
| 2,360,038 | 10/1944 | Burton | 417/145 |
| 3,224,638 | 12/1965 | Harrell | 222/64 |
| 3,609,379 | 9/1971 | Hildebrandt | 222/52 |

FOREIGN PATENT DOCUMENTS

806643 12/1936 France ...................................... 417/147

*Primary Examiner*—H. Grant Skaggs
*Attorney, Agent, or Firm*—Sprung, Felfe, Horn, Lynch & Kramer

[57] ABSTRACT

In an apparatus for the pulsewise dispensing of very small amounts of liquid controlled with a measuring instrument comprising an ejecting device for the pulsewise ejection of a desired amount of liquid, a pump is provided for supplying liquid to the vessel from a reservoir. The pump includes a neck portion having an inlet at the bottom thereof and a foot portion, with at least the foot portion immersed in a liquid contained in the reservoir. The foot portion has a volume at least as great as the refill volume of the measuring vessel and a feedline to the measuring vessel is disposed within the neck portion and terminates in proximity to the bottom of the foot portion. A check valve opens and closes the foot portion inlet by means of compressed gas which is controllable by sensing devices at the measuring vessel.

3 Claims, 3 Drawing Figures

APPARATUS FOR PULSEWISE DISPENSATION OF VERY SMALL AMOUNTS OF LIQUID, PARTICULARLY $H_2O_2$

The invention relates to an apparatus for the pulsewise dispensation of very small amounts (e.g., from 0.1 to 1 cm$^3$) of liquid, to be controlled by means of a metering device, particularly for use in a sterilizing apparatus working with $H_2O_2$, the metering device having a measuring vessel which is capable of being filled with a larger amount (e.g., from 5 to 15 cm$^3$) and whose outlet is connected to an ejaculating organ for the small amounts of liquid, the measuring vessel having between inlet and outlet a sensing means consisting of an upper sensor and a lower sensor which for the refilling of the measuring vessel with a defined amount of liquid from a large supply container through a feed line delivers a pulse to a pump, in accordance with U.S. application Ser. No. 880,527 filed Feb. 23, 1978.

In the Applicant's earlier patent application cited, mention is made of the problem that particularly in the sterilization of milk containers consisting of plastic-coated paperboard it is necessary to inject a very small amount of $H_2O_2$. In the case of a one-liter container, the normal amount is approximately 0.3 cm$^3$ while in the case of a half-liter carton it is approximately 0.2 cm$^3$. When too little $H_2O_2$ is injected, there is no assurance of complete sterilization, and when two much $H_2O_2$ is injected, consumption is needlessly increased and the milk with which the container is to be filled will be adversely affected. The earlier patent describes a species of design which makes it possible to accurately define, by means of a metering device, the small amount of liquid to be injected from a measuring vessel and assures uninterrupted drawing of the amount of liquid. To assure uninterrupted drawing, the measuring vessel of the metering device can be connected either to an elevated intermediate container or, through a pump, to a large supply container, and in particular to the large shipping container. The Applicant's in-plant experience has shown that refilling directly from the shipping container by means of a pump is more advantageous. Pumps of widely differing types may be used for such refilling. However, it has been found that the pumps used up to now are either very expensive, since their material of construction must be corrosion-resistant, or then susceptible to wear when they are constructed in the manner of a hose pump.

Based thereon, it is the object of the present further development to provide a pump permitting predetermined volumes of liquid to be pumped directly from the large supply container (shipping container) into the measuring vessel.

In accordance with the invention, this object is accomplished in that there is provided a pump comprising a neck and a foot and adapted to be immersed at least by the foot in the liquid contained in the supply container, and whose foot holds a volume of liquid coordinated with the defined refill quantity of the measuring vessel, the bottom of the foot having an inlet adapted to be closed by a check valve, the feed line to the measuring vessel terminating in proximity to the bottom, and compressed gas being admissible from above, through the neck of the pump, to act upon the filling volume of the foot. With this design, the neck may be connected to the compressed-air line through a solenoid valve, for example, so that as the pulse is triggered by the sensing means the compressed air forces the amount of liquid contained in the foot into the measuring vessel. The amount of liquid contained in the foot, plus a small amount in the neck, is limited by the liquid level in the supply container and by the termination of the feed line in the foot. However, as the liquid level in the supply container drops, the filling level in the pump changes. With a dropping liquid level in the storage tank, this gives rise to inaccuracies. To overcome this problem, it is advantageous for the neck of the pump to have a cross section several times smaller than that of the foot. The neck of the pump need only be large enough to permit the compressed air to be brought in a simple manner from above to the amount of liquid contained in the pump.

Moreover, it has been found that it is desirable for the filling volume of the foot to be larger than the refill quantity of the measuring vessel defined by the sensing means. The filling volume of the foot should be somewhat greater since the feed-line termination must be located slightly above the bottom of the foot or of the check valve so that a small residue of liquid remains in the foot. Moreover, allowance must be made for the fact that a certain amount of liquid may remain in the feed line. The prescribed small excess of the filling volume in the foot will compensate for these inaccuracies. To prevent that too much liquid is charged to the measuring vessel, the latter may advantageously be provided above the upper sensor with an overflow discharging into the supply container.

A design resulting in a compact construction is obtained when the feed line to the measuring vessel is routed through the neck of the pump. The foot may, specifically, consist of a cylindrical tube having a conical bottom, the check valve being disposed in the vertex of the bottom. The cross section of the foot should be as large as possible but small enough for the foot to pass readily through the opening in the supply container. A large cross section of the foot provides assurance that the supply container can be emptied almost completely by means of the immersible pump of simple design. For in the design in accordance with the invention the refill quantity is moved from the large supply container into the pump on the principle of communicating pipes, that is to say, pumping of a defined amount of liquid from the supply container is possible for as long as the liquid level is above the height of the foot (in other words, up to the neck of the pump).

In an advantageous embodiment the foot of the pump is in the form of a bend originating at the neck of the pump. The check valve preferably consists of a plastic disk which under the action of pressure applies itself in the interior of the foot of the pump as a seal against the inlet disposed at the front of the foot. The pump foot so constructed may be relatively long, and it may be helical, for example, particularly when the helix is of samll height, in order that the volume of the foot may be large in relation to that of the neck. This design results in a further simplification of the pump.

The design in accordance with the invention accomplishes a refilling of the measuring vessel wth defined amounts of liquid from the pump chamber by simple means, namely, filling of the pump on the principle of communicating pipes in combination with compressed air which acts upon the surface of the liquid. Costly pump systems or intermediate containers may be dispensed with.

Figure 2:
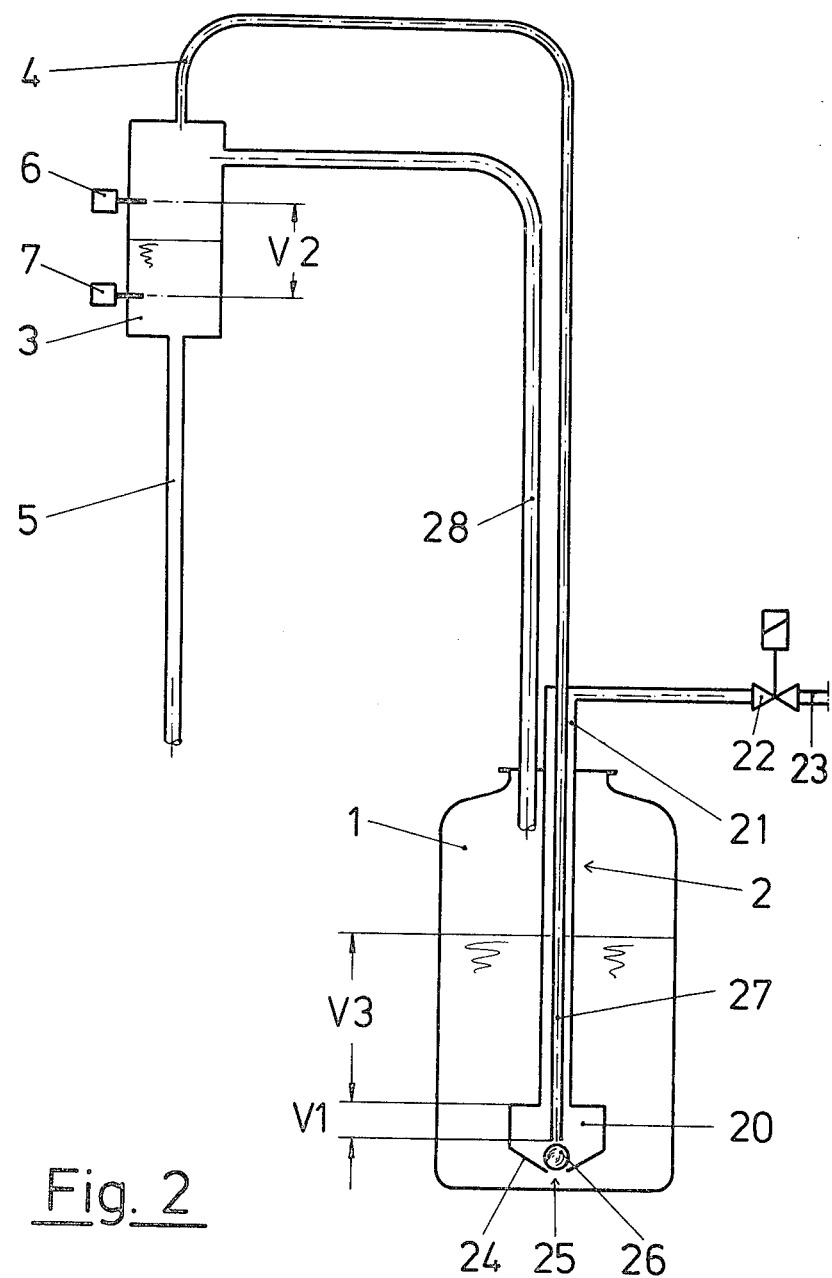
Figure 3:
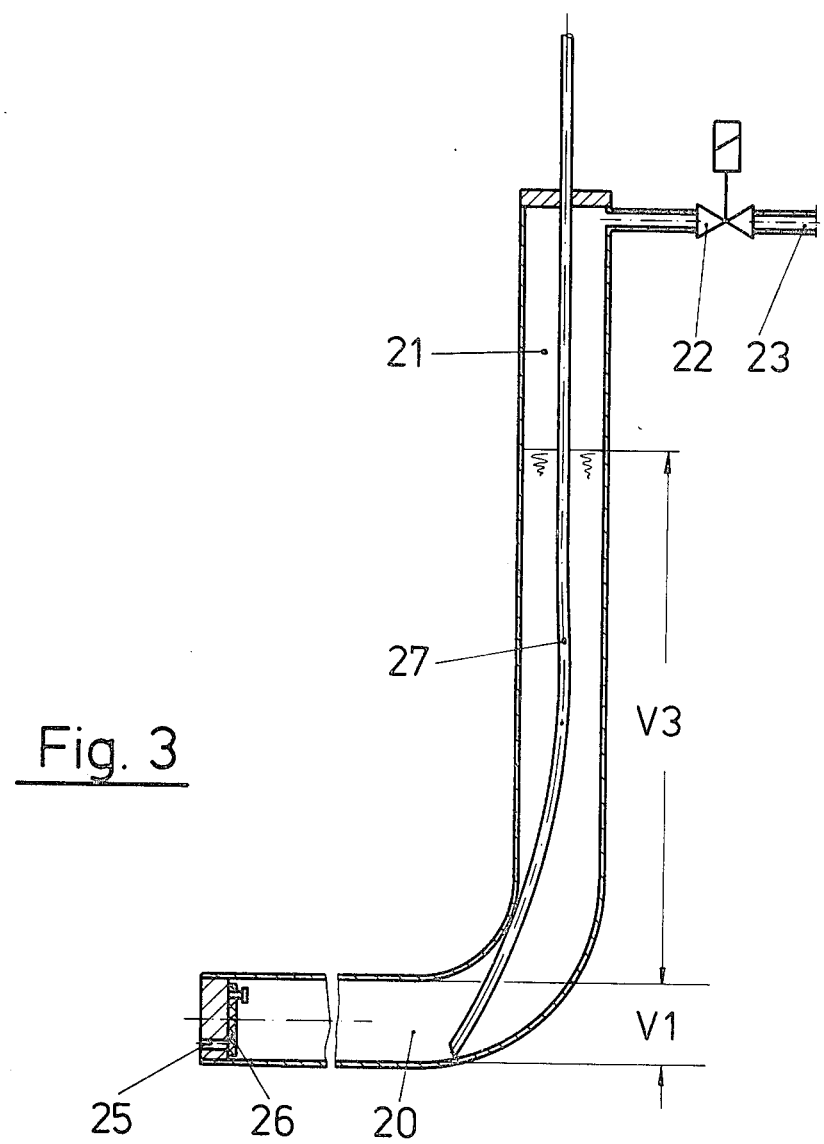

The invention is explained below in terms of an exemplified embodiment with reference to the drawing, where FIG. 1 is an overall view of the entire apparatus;
FIG. 2 is a diagrammatic representation of the pump on an enlarged scale; and
FIG. 3 is a diagrammatic representation on an enlarged scale of a modification of the pump.

A large supply container (shippping container) 1 contains $H_2O_2$ as sterilizing agent. From the supply container 1, an amount of liquid corresponding to the filling volume $V_1+V_3$ is moved by means of the pump 2 into the measuring vessel 3. The latter is provided between the inlet 4 and the outlet 5 with sensing means consisting of an upper sensor 6 and a lower sensor 7. The sensors 6 and 7 limit the volume of the refill quantity $V_2$, which may be 10 cm$^3$, for example. Through the outlet 5 of the measuring vessel 3, a very small amount of liquid, for example, 0.3 cm$^3$, is piped by means of an ejaculating organ 8 to the nozzle D. The ejaculating organ 8 is combined with a pulse generator 9 which with every very small amount of liquid ejaculated delivers a pulse to a pulse shaper 10. The latter is connected to a counter 11. Moreover, the sensing means 6,7 is connected to a start/stop device 12 which when refilling becomes necessary delivers a pulse to both a solenoid valve 22 of the pump 2 and the counter 11. The counter number of pulses is transmitted to a computer 13 which divides the volume of the known refill quantity $V_2$ by the number of pulses counted. In this way the computer furnishes the magnitude of the amount of liquid dispensed per ejaculation, and hence per carton. This value is transmitted to the indicating device 14 and to the comparators 15 and 16 for a maximum or minimum value. A relay 17 then triggers a signal when the respective extreme value is over- or undershot.

The design shown in FIG. 2, which provides for simple refilling of the measuring vessel 3 by means of the pump 2, merits special attention within the scope of the present invention. The pump, generally designated 2, consists essentially of a large-volume foot 20 and a slender neck 21 adapted to be connected to a compressed-air line 23 with interposition of a solenoid valve 22. In its bottom 24, which extends slightly conically downward, the front 20 has an inlet 25 adapted to be closed by a check valve 26. In the embodiment illustrated, the check valve 26 is a ball whose specific gravity is greater then the specific gravity of the liquid $H_2O_2$ in the supply container 1. A feed line 27 terminating in proximity to the bottom 24 is run through the neck 21 to the inlet 4 of the measuring vessel 3. Moreover, the measuring vessel communicates with the supply container 1 through an overflow 28.

The filling volume of the pump is determined by the vertical distance between the opening of the feed line 27 and the liquid vessel in the supply container 1 since the liquid contained in the supply containers 1 forces the liquid into the neck 21 of the pump 2 on the principle of communicating pipes. This filling volume is given by the sum of the volumes $V_1+V_3$; and since $V_3$ is very small in relation to $V_1$, the value $V_1+V_3$ is practically equal to the value $V_1$. When the pump 2 is immersed only by its foot, the value of $V_3$ is equal to zero. The filling volume $V_1+V_3$ should be somewhat greater than the refill quantity $V_2$ defined in the measuring vessel 3 between the upper sensor 6 and the lower sensor 7.

The design shown is distinguished by its simple operation. The pump 2 is immersed in the liquid $H_2O_2$ contained in the supply container 1. The $H_2O_2$ penetrates into the slender neck 21 of the pump 2. As soon as the liquid level in the measuring vessel 3 drops as far as the lower sensor 7, a pulse is delivered to the solenoid valve 22 with the result that the filling volume $V_1+V_3$ contained in the pump 2 is pumped into the measuring vessel 3 with the aid of compressed air. The solenoid valve 22 then closes as soon as the liquid level reaches the upper sensor 6. The solenoid valve is advantageously a three-way valve so that after the valve closes the compressed air contained in the neck is able to escape to the exterior and the liquid contained in the supply container 1 can again penetrate into the neck. The overflow 28 serves to conduct excess liquid from the measuring vessel 3 to the supply container. This may happen when the sensor 6 malfunctions. Moreover, the overflow 28 serves for the venting of the measuring vessel 3.

FIG. 3 shows a pump of modified design. At the lower end of the pump, the neck 21 passes into a bend which extends essentially horizontally and forms the foot 20. The latter is preferably made long in relation to the neck 21 of the pump and constructed as a helix, for example, in order to increase the volume ratio neck=$V_3$/foot=$V_1$ in favor of the neck. The volume $V_1$ should be greater than the defined refill quantity $V_2$ in the measuring vessel 3. The check valve 26 at the front end of the foot 20 is constructed as a plastic disk which applies itself as a seal against the inlet 25 as soon as the pressure in the interior of the foot 20 of the pump rises.

I claim:

1. In an apparatus for the pulsewise dispensing of very small amounts of liquid controlled with a measuring instrument comprising ejecting means for the pulsewise ejection of a desired amount of liquid, a measuring vessel having a volume greater than the volume of the liquid to be ejected for each pulse and having an inlet and an outlet connected to the ejecting means and wherein the cross section of the vessel is adapted to the amounts of liquid to be controlled, sensing means having an upper and a lower sensing device positioned at said vessel between the inlet and the outlet and defining a refill volume therebetween and responsive to the level of the liquid therein for generating a signal when the upper and lower sensing devices are activated, and a reservoir of liquid, the improvement comprising pumping means responsive to the sensing means for supplying a substantially constant amount of liquid from the reservoir to refill the vessel independent of the liquid level in the reservoir, the pumping means comprising a neck portion and a foot portion having an inlet at the bottom thereof, a feed line to the measuring vessel passing through the neck portion and having one end terminating in proximity to the bottom of the foot portion, at least the foot portion of the pumping means immersed in the liquid contained in the reservoir and wherein the foot portion has a volume substantially greater than that of the neck portion and slightly greater than the refill volume of the measuring vessel, a check valve for opening and closing the foot portion inlet, a supply of compressed gas controllable by the sensing means and applied to effect the opening of the check valve when shut off and to close the check valve and act upon the liquid in the foot portion of the pump to supply same to the measuring vessel when turned on, a three-way valve disposed between the neck portion of the pump and the supply of compressed-air and a start/stop device connected to the sensing means for controlling three-way valve in response to the signals received from the sensing means.

2. Apparatus as defined in claim 1, wherein the cross section of the neck portion of the pumping means is several times smaller than that of the foot portion of the pumping means.

3. Apparatus as defined in claim 1, wherein the foot portion of the pumping means is formed by a bend of the neck portion, and the check valve comprises a plastic disk which under the action of pressure applies itself in the interior of the foot portion as a seal against the inlet thereof.

* * * * *